(12) United States Patent
Darrow et al.

(10) Patent No.: US 6,201,980 B1
(45) Date of Patent: Mar. 13, 2001

(54) IMPLANTABLE MEDICAL SENSOR SYSTEM

(75) Inventors: Christopher B. Darrow, Pleasanton; Joe H. Satcher, Jr., Modesto; Stephen M. Lane, Oakland; Abraham P. Lee, Walnut Creek; Amy W. Wang, Berkeley, all of CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/166,236

(22) Filed: Oct. 5, 1998

(51) Int. Cl.[7] .................................................. A61B 5/05
(52) U.S. Cl. ............................................ 600/347; 600/345
(58) Field of Search .................................. 600/300–301, 600/316, 319, 323, 332, 339, 348, 361, 364–365, 345, 347; 128/903, 904, 897–899

(56) References Cited

U.S. PATENT DOCUMENTS

| | | |
|---|---|---|
| 4,114,606 | 9/1978 | Seylar . |
| 4,815,469 | 3/1989 | Cohen et al. . |
| 5,704,352 * | 1/1998 | Tremblay et al. .................. 600/300 |
| 5,709,225 | 1/1998 | Budgifvars et al. . |
| 5,711,861 * | 1/1998 | Ward et al. ........................ 600/347 |

OTHER PUBLICATIONS

Data Transmission from an Implantable Biotelemeter by Load–Shift Keying Using Circuit Configuration Modulator, Zhengnian Tang et al., 1995 IEEE, pp. 524–528.
Glucose–Sensing Electrode Coated With Polymer Complex Gel Containing Phenylboronic Acid, Akihiko Kikuchi et al., 1996 American Chemical Society, pp. 823–828.

* cited by examiner

Primary Examiner—Cary O'Connor
Assistant Examiner—Michael Astorino
(74) Attorney, Agent, or Firm—Alan H. Thompson; Daryl S. Grzybicki

(57) ABSTRACT

An implantable chemical sensor system for medical applications is described which permits selective recognition of an analyte using an expandable biocompatible sensor, such as a polymer, that undergoes a dimensional change in the presence of the analyte. The expandable polymer is incorporated into an electronic circuit component that changes its properties (e.g., frequency) when the polymer changes dimension. As the circuit changes its characteristics, an external interrogator transmits a signal transdermally to the transducer, and the concentration of the analyte is determined from the measured changes in the circuit. This invention may be used for minimally invasive monitoring of blood glucose levels in diabetic patients.

27 Claims, 5 Drawing Sheets

IMPLANTABLE MEDICAL SENSOR SYSTEM

The United States Government has rights in this invention pursuant to Contract No. W-7405-ENG-48 between the United States Department of Energy and the University of California for the operation of Lawrence Livermore National Laboratory.

BACKGROUND OF THE INVENTION

1. Field of the Invention

The present invention relates to an implantable medical device for continuous, minimally invasive monitoring of a chemical analyte of interest using an expandable, biocompatible material incorporated into an electronic circuit component that is interrogated transdermally.

2. Description of Related Art

Various implantable medical monitoring devices have been developed to measure internal physiological conditions of a patient. For example, an implantable medical sensor that determines the oxygen content of blood using a light-emitting diode and a phototransistor is described in U.S. Pat. No. 4,815,469 to Cohen et al. U.S. Pat. No. 5,709,225 to Budgifvars et al. describes a medical implant with a capacitive sensor, which is coated with a magnetically sensitive material that causes capacitance changes in the presence of a magnetic field.

Some medical devices use sensors coupled with frequency tuned L-C circuits, where the sensor mechanically translates the changes in the physiological condition to the inductor or capacitor of the tuned L-C circuit. An external transmitter detects the resulting changes in resonant frequency of the circuit. For example, U.S. Pat. No. 5,704,352 to Tremblay et al. describes an implantable passive biosensor for monitoring physiological conditions and converting the signals to digital format. In particular, the sensors are pressure transducers that detect the pressure of cerebrospinal fluid in the cavities of a patient's brain, which is useful for monitoring the operation of a cerebrospinal fluid shunt for treating hydrocephalus. U.S. Pat. No. 4,114,606 to Seylar describes an implantable device useful for monitoring intracranial pressure for the treatment of hypertension. The resonant frequency of the passive L-C circuit implanted in the cranium varies with changes in intracranial pressure. An external monitor interrogates and detects the frequency changes in the pressure transducer. Neither of these patents describes specific mechanisms or devices for transducing other physiological conditions.

The application of a transducer in an implantable medical device that reliably monitors changes in specific chemical analytes, such as blood glucose, would be advantageous. Blood glucose levels are of particular concern because diabetes is a chronic illness that affects more than 110 million people worldwide. Conventional therapy for the most severe form of diabetes, insulin-dependent diabetes mellitus (Type I), is to administer one or more injections per day of various forms of insulin, while monitoring blood glucose levels two or three times daily with commercial glucometers that require the withdrawal of blood samples. In practice, near normal blood sugar levels are difficult to maintain with this type of therapy due to the enormous inconvenience and day-to-day burden of conventional home-monitoring techniques. The resulting large fluctuations in blood glucose levels may be responsible for a number of serious secondary ailments commonly associated with diabetes, including stroke, liver and kidney damage, and loss of eyesight.

The present invention addresses the need for a convenient, minimally invasive medical sensor that provides continuous measurements of an analyte of interest using an expandable, biocompatible material incorporated into an electronic circuit element. More specifically, this invention will help diabetic patients in monitoring blood glucose levels and achieving tighter blood glucose control without requiring blood samples to be drawn.

SUMMARY OF THE INVENTION

The present invention provides an implantable sensor system for monitoring the concentration of a chemical analyte of interest. The invention is used for medical applications, such as implanted sensor packages for long-term monitoring of physiological blood or tissue analytes, like glucose for control of diabetes. The analyte concentration is transduced by a circuit, the characteristics (e.g., resonant frequency) of which are set by at least one circuit component (e.g., capacitance, inductance, resistance) whose value can be varied by the interaction between an analyte-sensitive material and the analyte. For example, changing the distance between the plates with a glucose-swellable polymer can vary the capacitance of a parallel-plate capacitor. As the electrical characteristics of the circuit vary in response to changes in the concentration of the analyte, an external interrogator transmits a signal transdermally to the transducer, and the concentration of the analyte is determined from the response of the transducer to that signal.

It is an object of the present invention to provide an implantable sensor system to monitor one or more chemical analytes of interest, including ionic species and molecular species. It is also an object to provide an implantable transducer having a circuit that requires no internal source of power, and which incorporates an expandable material that changes its dimensions in the presence of the analyte to influence the properties of the transducer circuit. Another object of the invention is to provide a sensor system interrogated transdermally by an external device to measure the characteristics of the circuit as the concentration of analyte changes. It is further an object of the invention to provide an implantable sensor system for monitoring the blood glucose levels in diabetic patients. Other objects and advantages of the present invention will become apparent from the following description and accompanying drawings.

BRIEF DESCRIPTION OF THE DRAWINGS

The accompanying drawings, which are incorporated into and form part of this disclosure, illustrate embodiments of the invention and together with the description, serve to explain the principles of the invention.

DETAILED DESCRIPTION OF THE INVENTION

The present invention is an implantable chemical sensor system for medical applications. The sensor system permits selective recognition of an analyte using an expandable biocompatible material, such as a polymer, which undergoes a dimensional change in response to changes in the concentration of the analyte of interest. The expandable polymer is incorporated into or mechanically connected to an electronic circuit element (e.g., capacitor, inductor, resistor) to cause a change in the value of that component, thereby altering the electrical characteristics of the circuit in a measurable way in response to changes in the analyte concentration. For example, changes induced in the value of a capacitor or inductor when the polymer changes dimension alter the resonant frequency of an L-C resonator circuit. Similarly, varying the value of a resistor leads to a measurable change in the R-C time constant of a discharging capacitor circuit.

Changes in the electrical characteristics of the circuit are detected transdermally from outside the body using an electronic interrogation device and then analyzed to determine the concentration of the analyte. Examples of transdermal interrogation methods include (1) frequency dependent electromagnetic loading of an interrogator antenna by a passive resonator sensor circuit, and (2) audio monitoring of a tone chirped by the voltage of discharging R-C circuit. In medical applications, it is generally desirable to have the implanted sensor circuits powered externally by the interrogator circuit, although the sensor circuits may also be designed for passive interrogation.

Figure 1:
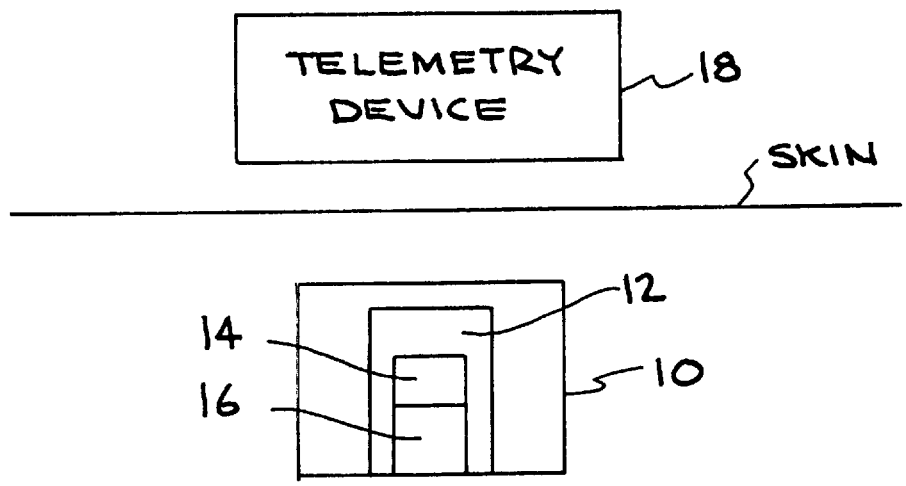
FIG. 1 shows an implantable chemical sensor system according to the present invention.

FIG. 1 shows a basic chemical sensor system according to the present invention. An implantable transducer package 10 includes a transducer circuit 12, which incorporates a circuit component 14 and a sensor 16 operably connected to the circuit component 14. A telemetry device 18 above the surface of the skin interrogates the implanted transducer circuit 12. The transducer package 10 is implanted subcutaneously, typically 2–4 mm below the surface of the skin, via a simple surgical procedure. The package 10 is miniaturized, typically about one centimeter in diameter. The implant comprises a biocompatible material that forms a hermetic (airtight) seal between the physiological environment and the electronic environment. The sensor circuit 12 may be mounted on a monolithic circuit board and contained within the hermetically sealed package 10.

Transduction of the analyte concentration is performed by the sensor 16, which maintains physical contact with the physiological environment while maintaining mechanical contact with at least one mechanically actuated circuit component 14 within the hermetically sealed package 10. The sensor 16 comprises a polymer that is designed (e.g., chemically altered) to undergo a (reversible) dimensional change (i.e., swelling, contraction) as the concentration of a selected analyte changes. Transduction occurs as a result of the mechanical action of the dimensional change of the sensor 16 being transferred to the mechanically actuated circuit component 14, thereby leading to a change in the electrical characteristics of the circuit 12.

Variations in the electrical properties (e.g., resonant frequency) of the circuit 12 induced by changes in the analyte concentration are detected and may be processed by the telemetry device 18, which is positioned near the implanted transducer package 10. The telemetry device 18 could be connected to a drug delivery system, so that when the measured analyte concentration reaches a pre-determined level, the system responds to a signal from the device 18 by delivering a pre-determined dosage of medication to the patient. The sensor system of the present invention can also be expanded to incorporate multiple circuits and multiple sensors/transducers in a single package to detect more than one analyte simultaneously or sequentially.

Polymers that are responsive to certain analytes are known in the art. The analytes may be molecular species such as sugars (glucose), urea, ammonia, enzymes, or narcotic substances, or ionic species (electrolytes) such as hydrogen ions (pH), alkaline earth ions, alkali metal ions, or transition metal ions. For example, Kikuchi et al. (*Anal. Chem.* Vol. 68, No. 5, March 1996), describe a glucose-swellable hydrogel (poly(DMAA-co-MAPB-co-DMAPAA-co-BMA)-PVA) that undergoes a reversible volumetric expansion in response to a change in glucose concentration. A volumetric expansion as high as $\Delta V/V \approx 30\%$ occurs in response to a change of glucose concentration of 200 mg/dL. This corresponds to a linear dimensional swelling of $\Delta r/r = 10\%$.

Figure 2:
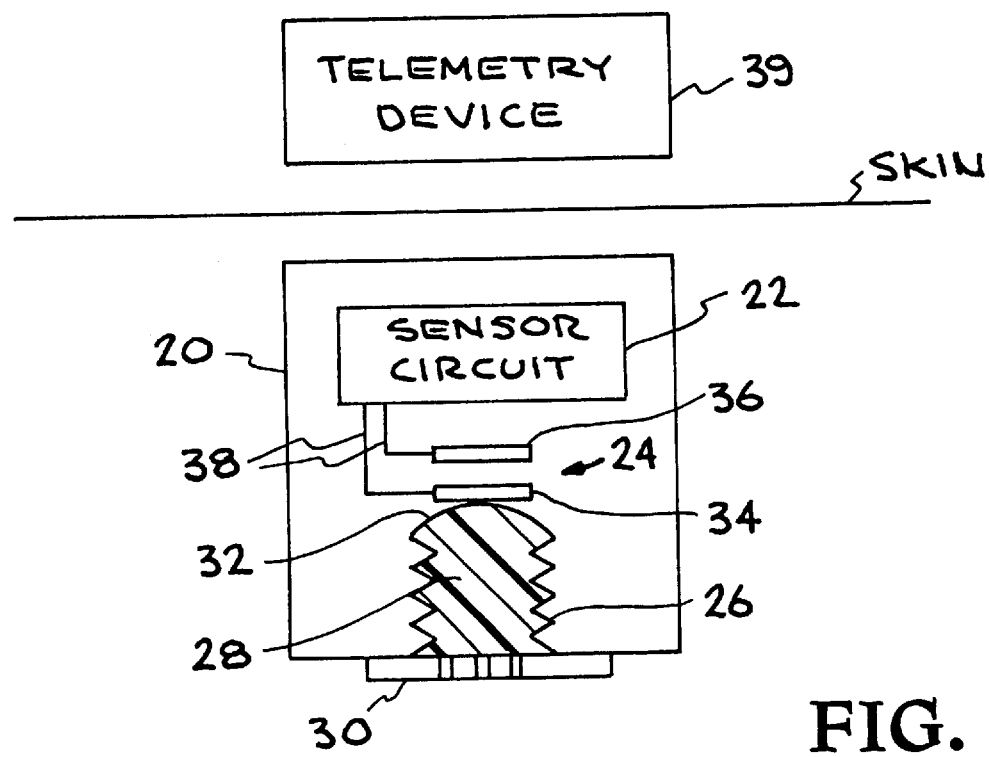
FIG. 2 shows an embodiment of the present invention in which the transducer is a variable capacitor.

Referring to FIG. 2, one embodiment of the invention is a subcutaneously implanted, biocompatible, hermetically sealed transducer package 20 containing a sensor circuit 22 that incorporates and is in electrical contact with a mechanically variable plate capacitor 24. The package 20 is formed to enclose the circuit 22 including the capacitor 24 and to create a housing for the sensor. In this embodiment, the housing is a pleated, expansible, bellows-shaped indentation or cavity 26 with a movable or deformable base 32. The bellows acts like a spring, with a reversible and predictable displacement for a given force. The axis of the bellows is normal to the surface of the package 20, and the cavity 26 may be several millimeters in diameter and approximately 1 mm deep. The cavity 26 is filled with an expandable polymer 28 and capped with a rigid, fine-pitch biocompatible material 30, such as a mesh, that allows perfusion of the polymer 28 by extracellular fluid, while mechanically constraining the analyte-sensitive polymer 28. As a result of this design, the swelling of the polymer 28 causes a measurable deflection of the base 32 of the bellows.

A planar conducting plate 34 is affixed to the deflectable or deformable base 32 of the bellows, and forms a parallel-plate capacitor with a second fixed planar conducting plate 36. Deflections of the base 32 of the bellows cause changes in the distance between the plates 34,36 of the capacitor, which results in an attendant change in capacitance. Some form of electrical connection, such as wire microbonds 38, connect the capacitor plates 34,36 to the circuit 22, so changes in the electrical properties of the circuit 22 are measured in response to changes in concentration of the analyte. Other configurations of the capacitor plates 34,36 in the transducer are possible, as long as the capacitance changes in response to the analyte-sensitive polymer. For example, the capacitor may comprise two fixed plates and a movable dielectric, where the sensor and dielectric are connected such that the changes in dimensions of the sensor cause relative motion of the dielectric and the plates, causing the capacitance of the capacitor to change.

Referring to FIG. 2, as the bellows 26 extends or contracts, the hermetic seal between the circuitry and the physiological environment is maintained. Variations in the electrical properties of the circuit 22 induced by changes in the analyte concentration are detected by a telemetry device 39 that is positioned outside the body, but near the implanted transducer package 20. The device 39 determines the analyte concentration by remotely determining the properties of the circuit 22 by evaluating a response of the transducer circuit obtained by electromagnetic, acoustic, or other means, to the applied interrogation signal. The results, having been read out transdermally, are presented on a display and archiving device, which can provide a continuous readout of the analyte concentration (e.g., mg/dL); the data may be recorded if desired (digital or analog format). The device 39 is preferably compact and portable, and may be a hand held device or worn on the body, like a wristwatch. Processing electronics within the device 39 may execute a stored program to evaluate and characterize the analyte-dependent data using known parameters of the transducer to determine the analyte concentration.

Figure 3:
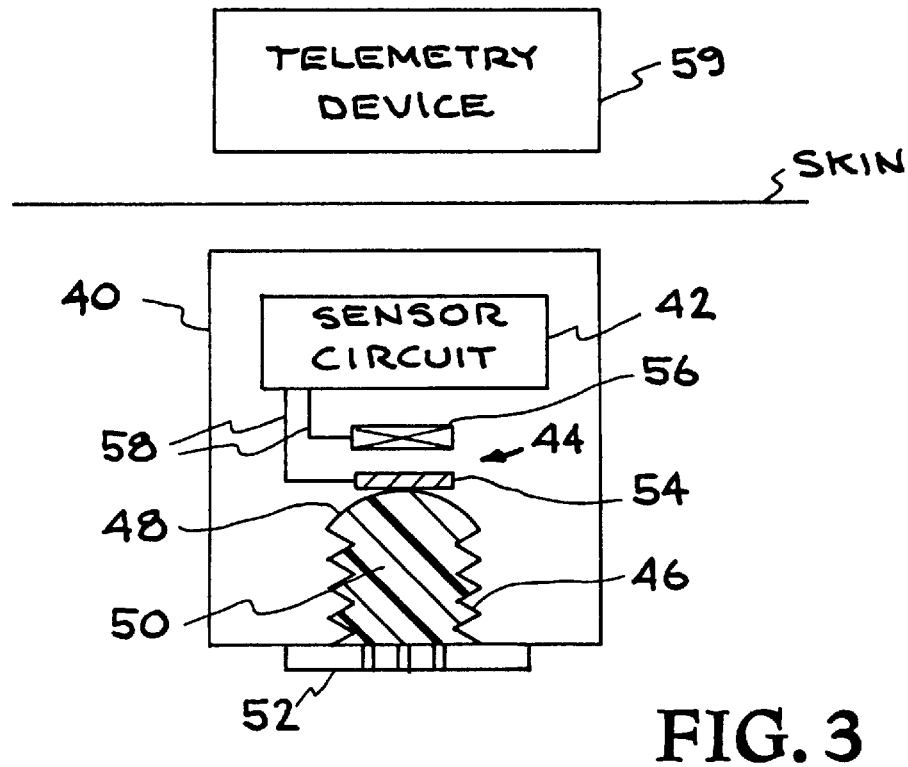
FIG. 3 shows an embodiment of the present invention in which the transducer is a variable inductor.

Referring to FIG. 3, a second embodiment of the invention shows a subcutaneously implanted, biocompatible, hermetically sealed transducer package 40 containing a circuit 42 that incorporates and is in electrical contact with a mechanically variable inductor 44. The package 40 is formed to enclose the circuit 42 including the inductor 44 and, as in FIG. 2, create a bellows-shaped cavity 46 with a deformable base 48. The axis of the bellows is normal to the surface of the package 40, and the cavity 46 may be several millimeters in diameter and approximately 1 mm deep. The cavity 46 is filled with an expandable polymer 50 and capped with a rigid, fine-pitch biocompatible plate or mesh 52 that allows perfusion of the sensor polymer 50 by extracellular fluid, while mechanically constraining the analyte-sensitive polymer 50. The expansion and contraction of the polymer 50 gives rise to a deflection of the base 48 of the bellows.

A disk 54 of magnetic material (e.g., ferrite) is affixed or in some manner connected to the deflectable or deformable base 48 of the bellows. The disk 54 forms an inductor 44 with a planar monolithic variable inductor coil 56, which is parallel to and in close proximity with the ferrite disk 54. Deflections of the base 48 of the bellows lead to changes in the distance between the disk 54 and the coil 56, which results in a change in the inductance of the inductor 44. The inductor 44 is electrically connected to the rest of the circuit 42, for example, by wire microbonds 58; so changes in the electrical properties of the circuit 42 are measured in response to changes in concentration of the analyte. Other configurations of the magnetic disk 54 and inductor coil 56 in the transducer are possible, as long as the inductance changes in response to the analyte-sensitive polymer.

As the sensor 50 changes dimensions, the hermetic seal between the circuitry and the physiological environment is maintained. Variations in the electrical properties of the circuit 42 induced by changes in the analyte concentration are detected by a telemetry device 59, such as that described for FIG. 2. The device 59 is positioned outside the body, but near the implanted transducer 40, and determines the analyte concentration by remotely determining the properties of the circuit by evaluating a response of the transducer circuit obtained by electromagnetic, acoustic, or other means, to the applied interrogation signal. The results, having been read out transdermally, are presented on a display and archiving device, which can provide a continuous readout of the analyte concentration and record these data if desired. The telemetry device 59 may also be connected to a drug delivery system.

Figure 4:
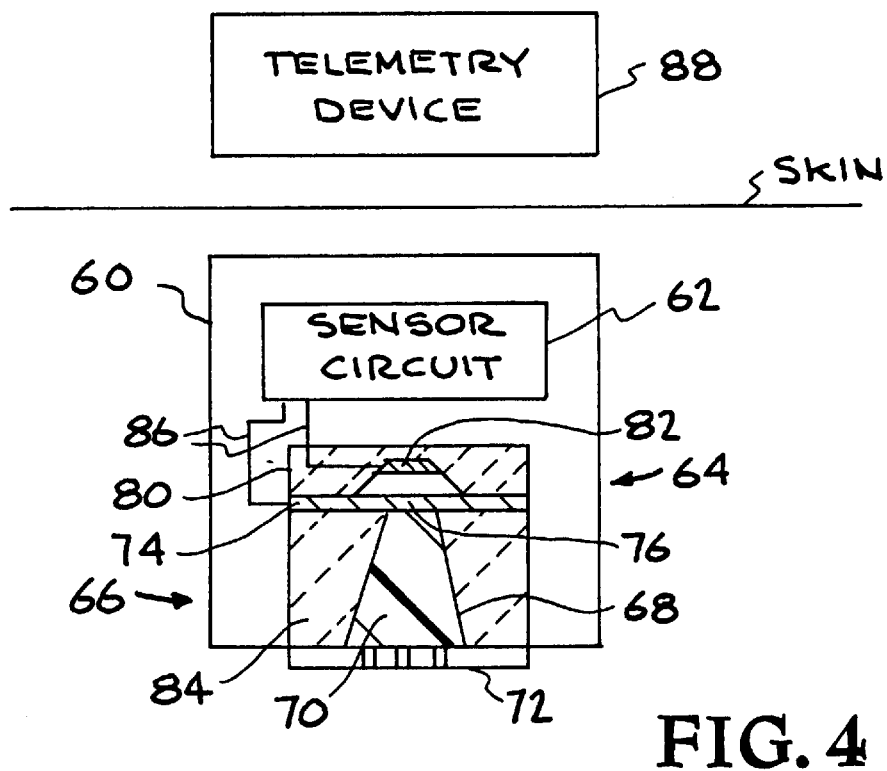
FIG. 4 shows an embodiment of the present invention in which the transducer is a variable capacitor formed with a micro-electromechanical system.

Referring to FIG. 4, another embodiment of the invention is a subcutaneously implanted, biocompatible, hermetically sealed transducer package 60 containing a sensor circuit 62 that incorporates and is in electrical contact with a mechanically variable plate capacitor 64. The package 60 is formed to hermetically enclose the circuit 62 including a micro electro-mechanical system (MEMS) transducer device 66. The MEMS device comprises a silicon micromachined well 68 filled with an expandable polymer 70 that swells or shrinks in the presence of the analyte of interest. The well 68 is bonded to and capped by a rigid, analyte-permeable grid chip 72 or retaining plate to mechanically constrain the polymer 70 in the well 68.

The well 68 may be formed by etching a silicon wafer 84, the opposite side of which has been deposited with a layer 74 of super-elastic conductive material, for example, a metal such as $Ni_x,Ti_x$. The etching process results in a well with a depth equal to the thickness of the silicon wafer. The conductive (metallic) layer 74 that remains after etching forms an elastic, deformable membrane 76 or diaphragm at the bottom of the well, which further serves as a hermetic seal between the physiological environment outside the package (on the polymer side of the membrane) and the electronic environment inside the package. Expansion (or contraction) of the sensor 70 gives rise to displacement or deflection of the membrane 76. The conductive layer 74 forming the deformable membrane 76 serves as one plate of the capacitor 64 and can extend only the length of the membrane 76, or beyond (as shown) if desired.

Figure 5:
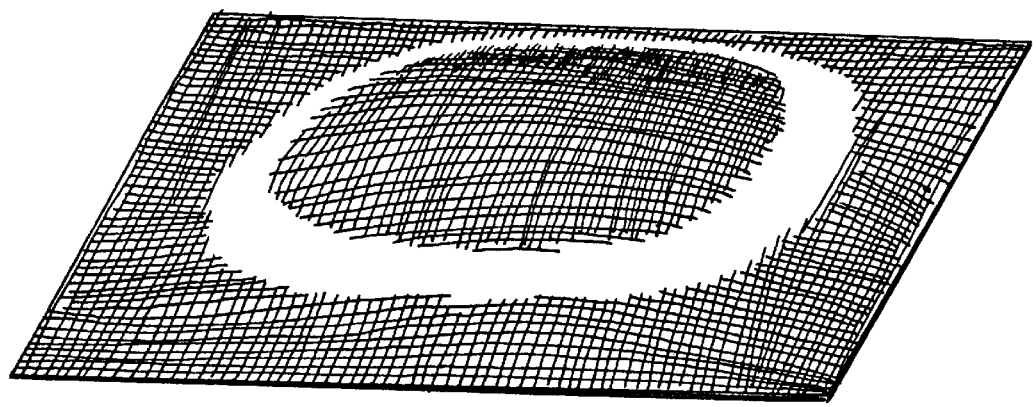
FIG. 5 shows the results of deformation measurements on an embodiment of the present invention.

FIG. 5 shows the results of deformation measurements on a mechanical prototype of the embodiment shown in FIG. 4. In this example, optical profilometry was used to demonstrate the extent of deflection (about 30 $\mu$m) of the membrane (4.0 mm×4.0 mm) in response to swelling of a P-HEMA hydrogel polymer by an ionic solution to which the polymer was exposed.

To complete the capacitor 64, a second planar conductive material is needed. FIG. 4 shows a possible configuration; a second silicon or glass wafer 80 is etched to form a well-defined recess, and a conductive (metallic) coating 82 is deposited on the bottom of the recess. The wafers 82,84 can be bonded together to form a parallel plate capacitor with a defined capacitor gap, where the capacitance is determined by the separation of the flexible membrane 76 and the conductive coating 82. The capacitor 64 is connected to the circuit 62, such as by wire microbonds 86 or by direct integration of the circuit. In an alternative embodiment of the invention, the deformable membrane MEMS actuator device can be configured to form a variable planar inductor (as in FIG. 3), instead of a capacitor.

As the sensor 70 changes dimensions and displaces the membrane 76, the seal formed by the membrane 76 between the circuit 62 and the physiological environment is maintained. Variations in the electrical properties of the circuit 62 induced by changes in the analyte concentration are detected by a telemetry device 88 that is positioned outside the body, but near the implanted transducer 60. The interrogation device 88 determines the analyte concentration by remotely determining the properties of the circuit by evaluating a response of the transducer circuit obtained by electromagnetic, acoustic, or other means, to the applied interrogation signal. Processing electronics within the device 88 may execute a stored program to evaluate and characterize the analyte-dependent data using known parameters of the transducer to determine the analyte concentration. The results are read out transdermally and presented on a display and archiving device, which can provide a continuous readout of the analyte concentration and record these data if desired.

Figure 6:
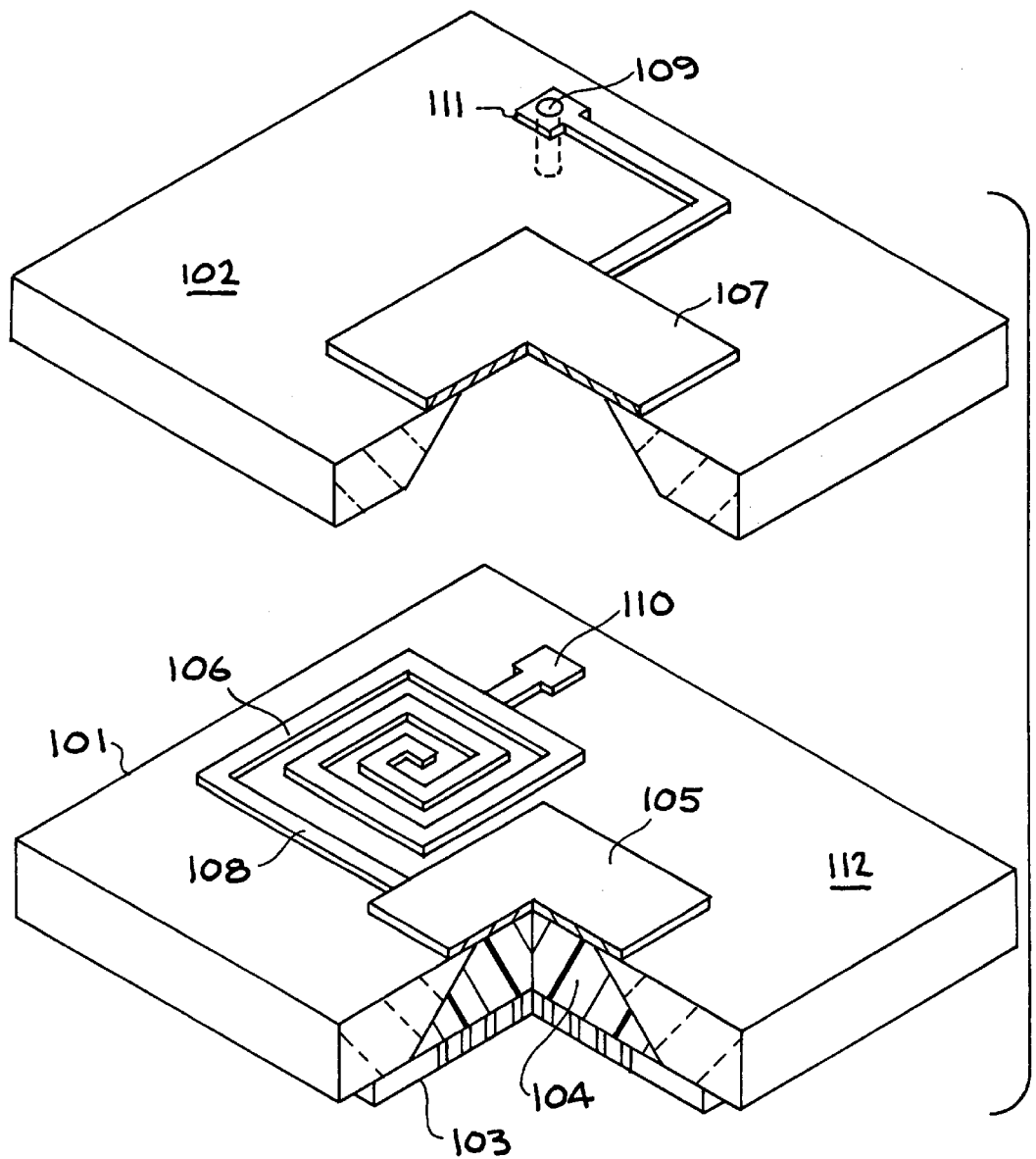
FIG. 6 shows a MEMS assembly configured to form the transducer according to the present invention.

Further integration of the variable circuit component with the other required circuit elements for a variable capacitor MEMS sensor, such as depicted in FIG. 6, may be advantageous from a manufacturing standpoint. The MEMS-based capacitor (or inductor) can be directly fabricated on a wafer (or wafers) with other required circuit components, to form an integrated, MEMS-based implantable transducer circuit.

FIG. 6 illustrates an embodiment of an integrated MEMS assembly formed from two subassemblies 101,102. The first (lower) subassembly 101 comprises a well 104 filled with an analyte-sensitive polymer that expands and contracts in response to the analyte. A rigid retaining mesh 103 allows permeation of the polymer by the analyte-containing fluid. A flexible, deformable conductive membrane 105 is patterned on the top surface 112 facing the second (upper) subassembly 102. Also patterned on this top surface 112 is a planar inductor coil 106 that is electrically connected to the movable capacitor membrane 105 on the first subassembly 101 and to a fixed capacitor plate 107 on the second subassembly 102. Electrical contact from the coil 106 to the movable capacitor membrane 105 can be made through a patterned trace 108. Electrical contact to the fixed plate 107 can be made by a conductive via 109 that connects a first (lower) subcircuit pad 110 and a second (upper) subcircuit pad 111. The pads 110,111 are connected upon assembly of the first and second subassemblies 101,102, thereby completing the L-C circuit of this embodiment.

Figure 7:
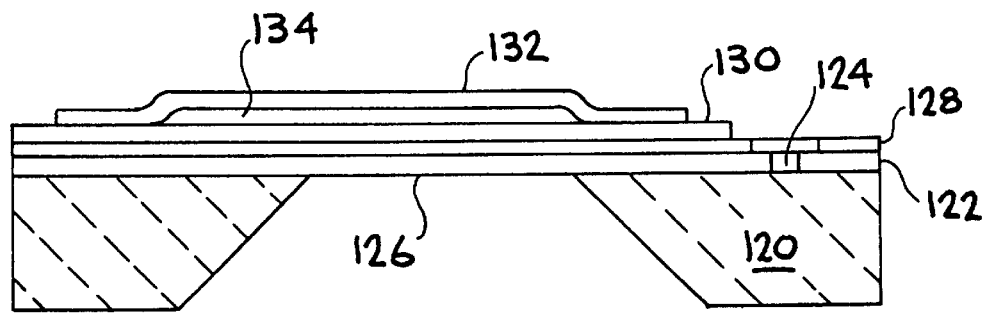
FIG. 7 shows a MEMS assembly fabricated by surface micromachining according to the present invention.

FIG. 7 illustrates an alternative configuration of FIG. 4, where the opposing electrode (capacitor plate) is surface micromachined instead of bulk micromachined and bonded. By polysilicon surface micromachining, an opposing electrode can be integrated on the opposite side of the flexible membrane through a batch process, resulting in lower cost and smaller size of the overall device. This type of design will also provide a much smaller gap (<1000 Å) for higher measurement sensitivity.

The fabrication process includes the low pressure vapor deposition of a silicon nitride layer 122 and patterning of grounding feedthroughs 124. A silicon nitride membrane 126 is then formed by patterning and anisotropially etching from the backside of the silicon substrate 120. A thin film 128 shape memory alloy (SMA) (e.g., Ti—Ni) is deposited on the front side to enhance toughness of the silicon nitride membrane 126. Electrical feedthrough from the SMA film 128 to the ground substrate 120 is established through the silicon nitride opening 124. A second silicon nitride layer 130 with a thickness of 100 Å–1000 Å is deposited on top of the SMA film 128 for insulation between the opposing electrode layers 128 and 132. A polycrystalline silicon layer 132 is deposited over a sacrificial $SiO_2$ layer 134 to form the top electrode. The sacrificial layer 134 (e.g., $SiO_2$ or glass), with a thickness of about 0.5 $\mu$m to 2 $\mu$m, is deposited on top of the silicon nitride layer 130 and patterned to form the gap 134 between the electrodes 128,132. The sacrificial layer 134 is later selectively etched away with etchants such as buffered hydrofluoride.

Figure 8:
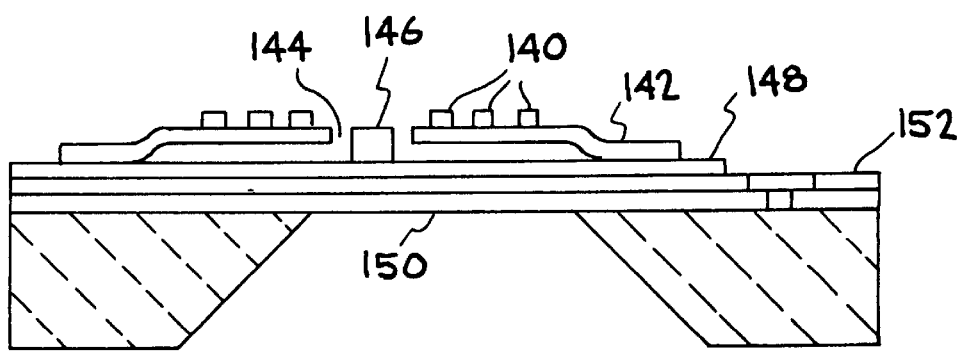
FIG. 8 shows a MEMS assembly fabricated by surface micromachining according to the present invention.

FIG. 8 is an embodiment of the present invention that relies on inductance change rather than capacitance change and utilizes the same fabrication techniques as in FIG. 7. In this embodiment, a spiral thin film metal inductor 140 is patterned on the top electrode 142. A hole 144 is patterned in the top electrode 142, and a pedestal 146 made of a magnetic material is patterned on the insulating nitride layer 148. The insulating layer 148 overlays the flexible membrane 150 and its support layer 152. When the membrane 150 moves in response to dimensional changes of the analyte-sensitive polymer (not shown), the pedestal 146 patterned on top of the moving membrane moves through the inductor coil 140, causing an inductance change. The change in inductance is then detected by an external telemetry device, as described previously.

Figure 9:
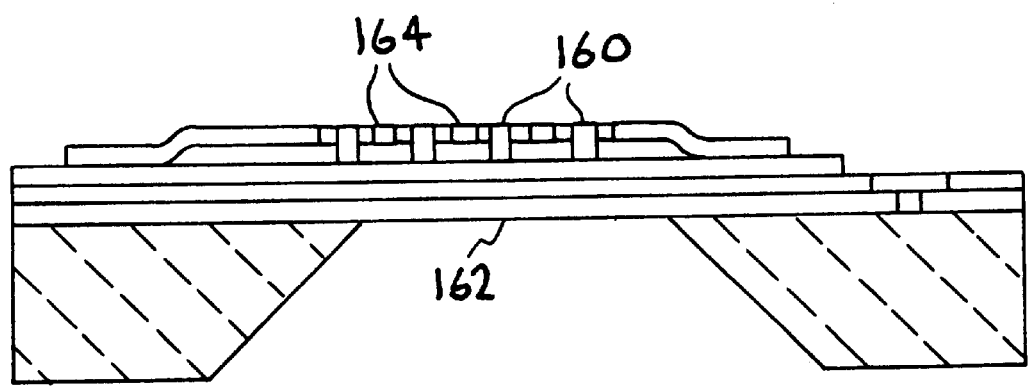
FIG. 9 shows a MEMS assembly fabricated by surface micromachining according to the present invention.

FIG. 9 is another capacitive sensing configuration fabricated using surface micromachining techniques. This embodiment includes moving comb pedestals 160 that are patterned on top of the moving membrane 162. The pedestals 160 are situated to move through static comb fingers 164 that are isolated from the movement of the membrane 162. As the pedestals 160 move through the fingers 164, the capacitive change (and therefore displacement of the moving membrane 162) is detected. The pedestals 160 and fingers 164 are made of conductive material, such as polysilicon or a metal (e.g., Al, Au). The advantage of this configuration is that the capacitance change is proportional to displacement and independent of the position. This simplifies the circuitry design from the parallel plate configuration of FIG. 7.

The foregoing description of preferred embodiments of the invention is presented for purposes of illustration and description and is not intended to be exhaustive or to limit the invention to the precise form disclosed. Many modifications and variations are possible in light of the above teaching.

What is claimed is:

1. An implantable chemical sensor system for measuring the concentration of an analyte of interest, comprising:
   a sensor, comprising a material that selectively responds to an analyte of interest by changing its dimensions;
   an implantable transducer, comprising an electronic circuit having at least one variable electrical characteristic that changes in response to dimensional changes of the sensor; and
   a telemetry device that interrogates the transducer transdermally to measure the changes in the electrical characteristic of the circuit as the concentration of analyte changes.

2. The sensor system as recited in claim 1, wherein the circuit comprises at least one mechanically actuated circuit component, wherein the dimensional changes of the sensor are used to mechanically actuate changes in the circuit component.

3. The sensor system as recited in claim 2, wherein the circuit component comprises a variable capacitor.

4. The sensor system as recited in claim 3, wherein the capacitor comprises two plates, wherein at least one plate moves relative to the other in response to the sensor changing its dimensions.

5. The sensor system as recited in claim 4, wherein the transducer further comprises an area that moves in response to the sensor changing dimensions and that is connected to at least one plate.

6. The sensor system as recited in claim 1, wherein the transducer further comprises a housing for the sensor, including an area that moves in response to the sensor changing dimensions, and including a rigid, analyte-permeable material that constrains the sensor in the housing.

7. The sensor system as recited in claim 6, wherein the area that moves is a pleated, expansible area.

8. The sensor system as recited in claim 3, wherein the capacitor comprises two fixed plates and a movable dielectric, wherein changes in dimensions of the sensor cause relative motion of the dielectric and the plates, whereby the capacitance of the capacitor changes.

9. The sensor system as recited in claim 2, wherein the circuit component comprises a variable inductor.

10. The sensor system as recited in claim 9, wherein the inductor comprises an inductance coil, and the coil's inductance changes in response to the sensor changing its dimensions.

11. The sensor system as recited in claim 10, further comprising a magnetic material that moves in response to the sensor changing its dimensions.

12. The sensor system as recited in claim 9, wherein the inductor comprises an inductance coil and a magnetic material, wherein at least one of the coil and magnetic material move relative to the other, and the coil's inductance changes in response to the sensor changing its dimensions.

13. The sensor system as recited in claim 1, wherein the sensor comprises a polymer capable of reversibly expanding and contracting in volume in the presence of the analyte.

14. The sensor system as recited in claim 1, wherein the sensor comprises a hydrogel that changes dimensions in the presence of glucose.

15. The sensor system as recited in claim 1, wherein the sensor responds to at least one analyte selected from the group consisting of sugars, urea, ammonia, hydrogen ions, alkaline earth ions, alkali metal ions, transition metal ions, enzymes, and narcotic substances.

16. The sensor system as recited in claim 2, wherein the circuit component comprises a micro electromechanical system (MEMS) device.

17. The sensor system as recited in claim 16, wherein the MEMS device comprises a cavity into which the sensor is situated, and a flexible conductive membrane covering a portion of the cavity such that the membrane moves in response to the sensor changing its dimensions.

18. The sensor system as recited in claim 17, wherein the transducer includes a planar conductive material, wherein the planar material and the membrane comprise plates of a capacitor, wherein the capacitor's capacitance changes in response to the sensor changing its dimensions.

19. The sensor system as recited in claim 18, wherein the planar conductive material is deposited on a surface of an etchable substrate.

20. The sensor system as recited in claim 19, wherein a well is formed on the surface of the substrate, and the conductive material is deposited thereon.

21. The sensor system as recited in claim 17, wherein the MEMS device comprises at least one variable circuit component comprising a variable capacitor, the capacitance of which varies in response to deflections of the membrane.

22. The sensor system as recited in claim 21, wherein the MEMS device further comprises an integrated inductor.

23. The sensor system as recited in claim 17, wherein the MEMS device comprises at least one variable circuit component comprising a variable inductor, wherein the inductor comprises an inductor coil and a magnetic material that moves with the membrane.

24. The sensor system as recited in claim 1, wherein the circuit comprises a micro electromechanical system (MEMS) device which further comprises at least one variable circuit component co-fabricated with other circuit elements to form an integrated MEMS assembly.

25. The sensor system as recited in claim 1, wherein telemetry device measures the resonant frequency of the transducer circuit.

26. The sensor system as recited in claim 1, wherein telemetry device measures an acoustic tone, the frequency of which is moderated by the transducer circuit.

27. A method for measuring the concentration of an analyte of interest using an implantable sensor system, comprising:

providing a transducer, comprising an electronic circuit and a sensor, wherein the sensor comprises a material that selectively responds to an analyte of interest by changing its dimensions, and wherein the circuit has at least one variable electrical characteristic that changes in response to dimensional changes of the sensor;

implanting the transducer subcutaneously into a patient; and providing a telemetry device that interrogates the transducer transdermally to measure the changes in the electrical characteristic of the circuit as the concentration of analyte changes.

* * * * *